(12) United States Patent
Rostykus et al.

(10) Patent No.: US 12,285,225 B2
(45) Date of Patent: Apr. 29, 2025

(54) MEDICAL IMAGING CONTROL APPARATUS, MEDICAL IMAGING SYSTEM AND METHOD OF OPERATING A MEDICAL IMAGING SYSTEM

(71) Applicant: LEICA INSTRUMENTS (SINGAPORE) PTE. LTD., Singapore (SG)

(72) Inventors: Manon Rostykus, Vulliens (CH); Wei Thiam Neo, Singapore (SG)

(73) Assignee: LEICA INSTRUMENTS (SINGAPORE) PTE. LTD., Singapore (SG)

( * ) Notice: Subject to any disclaimer, the term of this patent is extended or adjusted under 35 U.S.C. 154(b) by 11 days.

(21) Appl. No.: 18/201,980

(22) Filed: May 25, 2023

(65) Prior Publication Data
US 2023/0380912 A1 Nov. 30, 2023

(30) Foreign Application Priority Data
May 27, 2022 (EP) ..................................... 22175904

(51) Int. Cl.
*A61B 34/00* (2016.01)
*A61B 90/00* (2016.01)
(Continued)

(52) U.S. Cl.
CPC .............. *A61B 34/25* (2016.02); *A61B 90/20* (2016.02); *A61B 90/37* (2016.02); *G06T 3/60* (2013.01);
(Continued)

(58) Field of Classification Search
CPC . A61B 90/37; A61B 1/00009; A61B 1/00045; A61B 1/04; A61B 1/045;
(Continued)

(56) References Cited

U.S. PATENT DOCUMENTS 6,636,254 B1 10/2003 Onishi et al.
2008/0103354 A1 5/2008 Kim
(Continued)

FOREIGN PATENT DOCUMENTS

DE 9301434 U1 5/1993
DE 102015216648 B3 11/2016
(Continued)

*Primary Examiner* — Nam D Pham
(74) *Attorney, Agent, or Firm* — Hodgson Russ LLP

(57) ABSTRACT

A medical imaging control apparatus comprising a data input interface which is configured to receive electronic image data representing an original image of an object, a processor which is configured to process electronic image data received at the data input interface such that when the electronic image data is used to generate an image the image generated is the original image rotated through an angle of rotation, a plurality of data output interfaces via which processed electronic image data from the processor can be provided to a display so that the processed electronic image data can be used to generate an image, a user interface configured with a plurality of user-selectable element which are configured to be operable by a user to select one of the data output interfaces and to assign to the user-selected data output interface the user-selected angle of rotation; and a controller configured to control the transmission of electronic image data via the user-selected data output interface, wherein the electronic image data transmitted via the user-selected data output interface has been processed by the processor such that when the electronic image data is used to generate an electronic image the image generated is the original image rotated through the user-selected angle of rotation assigned to that user-selected data output interface.

13 Claims, 6 Drawing Sheets

Figure 1:
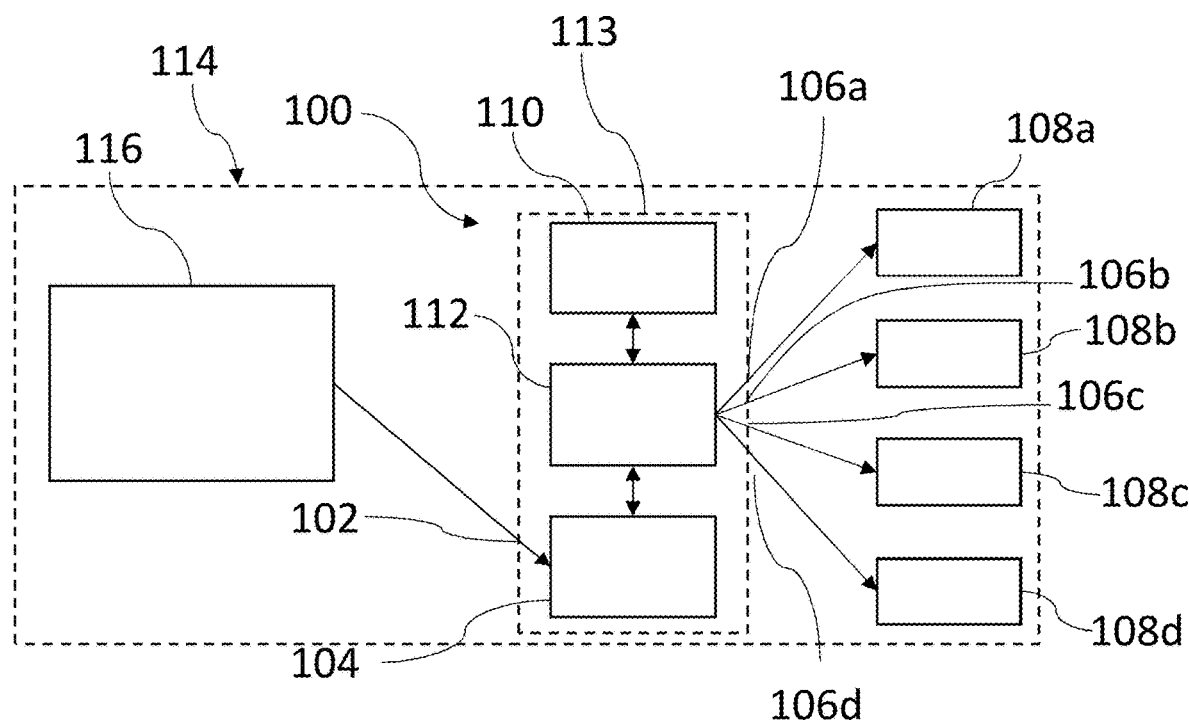

(51) Int. Cl.
  *A61B 90/20* (2016.01)
  *A61B 90/50* (2016.01)
  *G06T 3/60* (2024.01)
  *H04N 5/57* (2006.01)

(52) U.S. Cl.
  CPC .......... *H04N 5/57* (2013.01); *A61B 2090/502* (2016.02)

(58) Field of Classification Search
  CPC ............ A61B 2034/258; G02B 27/017; G02B 21/365; G06F 3/0482; G06T 3/60; H04N 5/57
  See application file for complete search history.

(56) References Cited

U.S. PATENT DOCUMENTS

| | | | |
|---|---|---|---|
| 2016/0062636 A1* | 3/2016 | Jung | .................. G06F 3/04817 715/762 |
| 2017/0151034 A1 | 6/2017 | Oda et al. | |
| 2019/0282063 A1* | 9/2019 | Kado | ..................... G16H 30/40 |
| 2020/0068142 A1 | 2/2020 | Ueda | |
| 2020/0333578 A1 | 10/2020 | Capelli et al. | |
| 2021/0215932 A1 | 7/2021 | Mair et al. | |

FOREIGN PATENT DOCUMENTS

| | | |
|---|---|---|
| JP | H10323325 A | 12/1998 |
| WO | 2021224404 A1 | 11/2021 |

* cited by examiner

MEDICAL IMAGING CONTROL APPARATUS, MEDICAL IMAGING SYSTEM AND METHOD OF OPERATING A MEDICAL IMAGING SYSTEM

CROSS REFERENCE TO RELATED APPLICATIONS

This application claims priority of European patent application number 22175904.6 filed May 27, 2022, the entire disclosure of which is incorporated by reference herein.

TECHNICAL FIELD

This disclosure relates to medical imaging apparatus, medical imaging system and method of operating a medical imaging system, in particular to an apparatus, system and method for use in surgery.

BACKGROUND

It is known to use a medical imaging system to assist a surgeon in carrying out delicate surgical procedures, to provide enlarged images of the operating site and/or record images of the surgery. Such a system may comprise a microscope and a digital video camera which captures images from the microscope, and an image transmission device which transmits the images from the video camera to a head-mounted display worn by a surgeon or surgeon's assistant and/or to an external screen. Examples of such systems are described in WO2018/170522, EP3848779, and WO2021/224404.

SUMMARY

According to one aspect of the disclosed technology we provide a medical imaging control apparatus comprising:
  a. a data input interface which is configured to receive electronic image data representing an original image of an object,
  b. a processor which is configured to process electronic image data received at the data input interface such that when the electronic image data is used to generate an image the image generated is the original image rotated through an angle of rotation,
  c. a plurality of data output interfaces via which processed electronic image data from the processor can be provided to a display so that the processed electronic image data can be used to generate an image,
  d. a user interface configured with a plurality of user-selectable elements which are configured to be operable by a user to select one of the data output interfaces and to assign to the user-selected data output interface the user-selected angle of rotation; and
  e. a controller configured to control the transmission of electronic image data via the user-selected data output interface, wherein the electronic image data transmitted via the user-selected data output interface has been processed by the processor such that when the electronic image data is used to generate an electronic image the image generated is the original image rotated through the user-selected angle of rotation assigned to that user-selected data output interface.

In one embodiment, the processor is configured to process electronic image data received at the data input interface such that when the electronic image data is used to generate an image the image generated is the original image rotated through one of a plurality of predetermined angles of rotation, and the plurality of user-selectable elements are configured to be operable by a user to select one of the data output interfaces and to assign to the user-selected data output interface one of the predetermined angles of rotation.

In one embodiment, the predetermined angles of rotation include 0°.

In one embodiment, the predetermined angles of rotation include 90°, 180°, and 270°.

In one embodiment each of the user-selectable elements is associated with either one of the data output interfaces or one of the predetermined angles of rotation.

The processor may be configured to process the electronic image data to change the brightness level of an image generated from the electronic image data. In this case, the user interface may further comprise a brightness control element which is configured to be operable by a user to select a brightness level for the electronic image data to be transmitted via the user-selected data output interface, and the controller be configured to control the transmission via the user-selected data output interface of the electronic image data at the user-selected brightness level.

In one embodiment, the data input interface is configured to receive electronic image data which can be used to generate an image stream.

In one embodiment, the processor, user interface and controller are provided in a housing.

In one embodiment, the data input interface comprises a port provided in the housing and is configured to be connected to a data transfer cable.

In one embodiment, the data output interfaces each comprise a port provided in the housing and is configured to be connected to a data transfer cable.

In one embodiment, the user interface comprises a plurality of interfaces provided on separate devices.

According to another aspect of the disclosed technology we provide a medical imaging system comprising a medical imaging control apparatus having any feature or combination of features mentioned above, the system further comprising a microscope, wherein the data input interface of the medical imaging control apparatus is connected to the microscope such that electronics image data generated by the microscope is received by the data input interface.

In one embodiment, the system further comprises a plurality of displays each of which is connected to one of the data output interfaces and configured to receive electronic image data from the data output interface to which it is connected to use the received electronic image data to generate an image or image stream.

In one embodiment each display is part of a head-mounted display device.

According to another aspect of the disclosed technology we provide a medical imaging system comprising a medical imaging control apparatus having any features or combination of features mentioned above, the system further comprising a plurality of displays each of which is connected to one of the data output interfaces and configured to receive electronic image data from the data output interface to which it is connected to use the received electronic image data to generate an image or image stream.

In one embodiment, each display is part of a head-mounted display device.

According to another aspect of the disclosed technology we provide method of operating a medical imaging system comprising acquiring electronic image data representing an original image of an object, enabling a user to select one of a plurality of data output interfaces and to assign to the selected data output interface one of a plurality of predetermined angles of rotation, processing the image data such that when the processed image data is used to generate an image the image generated is the original image rotated through the predetermined angle of rotation assigned to the user-selected data output interface, and transmitting the processed image data to the user-selected data output interface.

According to another aspect of the disclosed technology we provide a computer program product comprising program code stored on a machine-readable medium, the computer program being configured to carry out the method of operating a medical imaging system described above when the computer program runs on a computer system of the medical imaging system.

SHORT DESCRIPTION OF THE FIGURES

Figure 2:
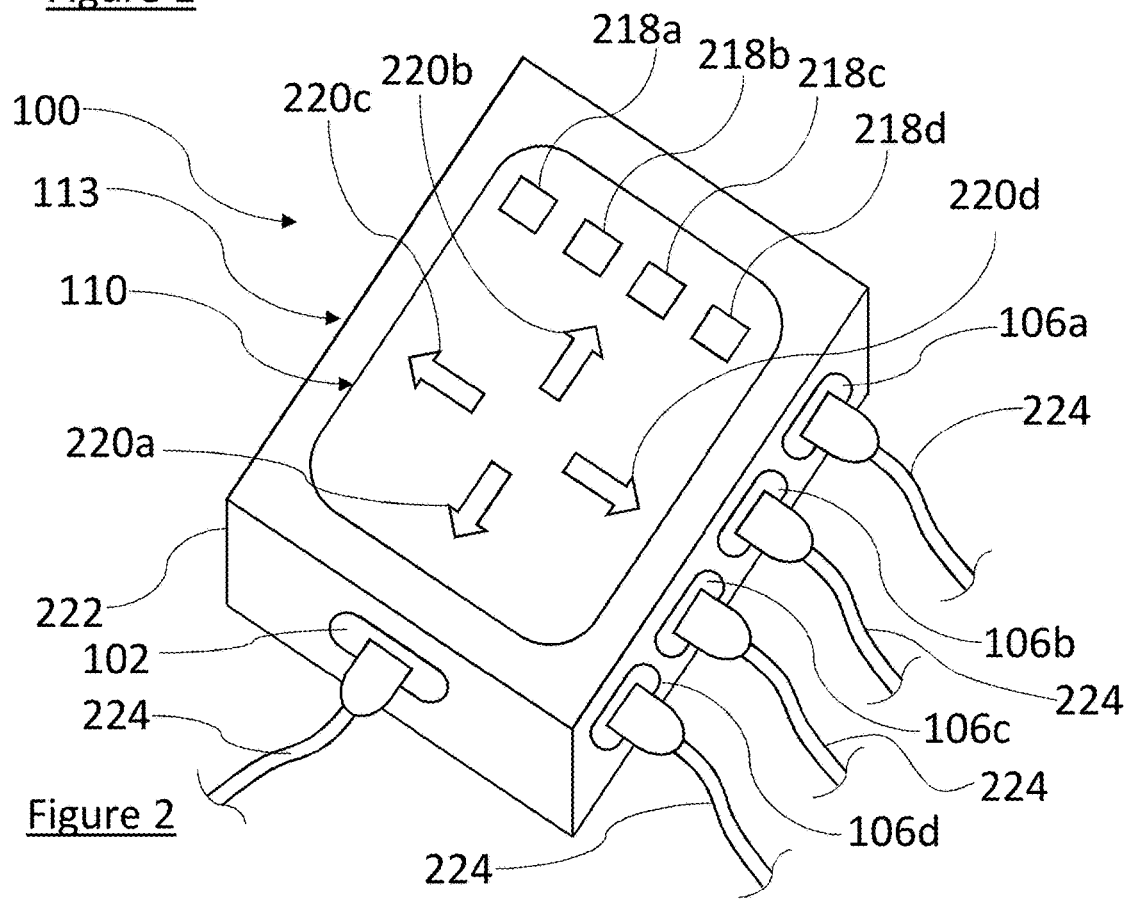
Figure 3:
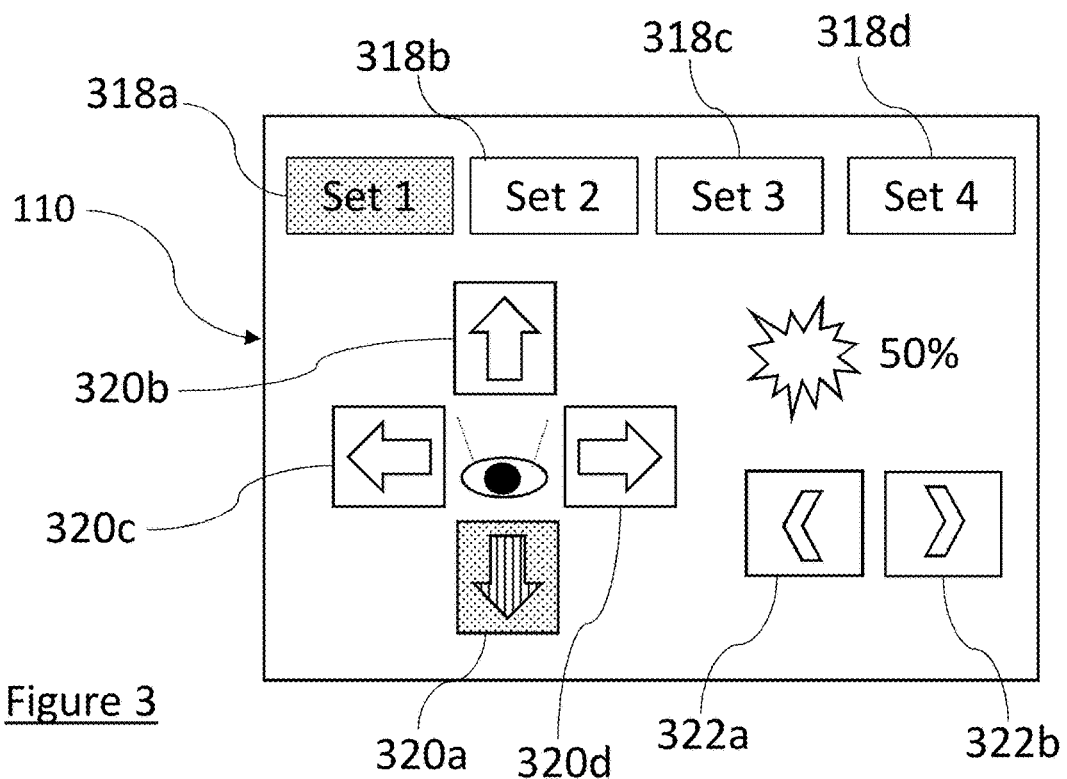
Figure 4:
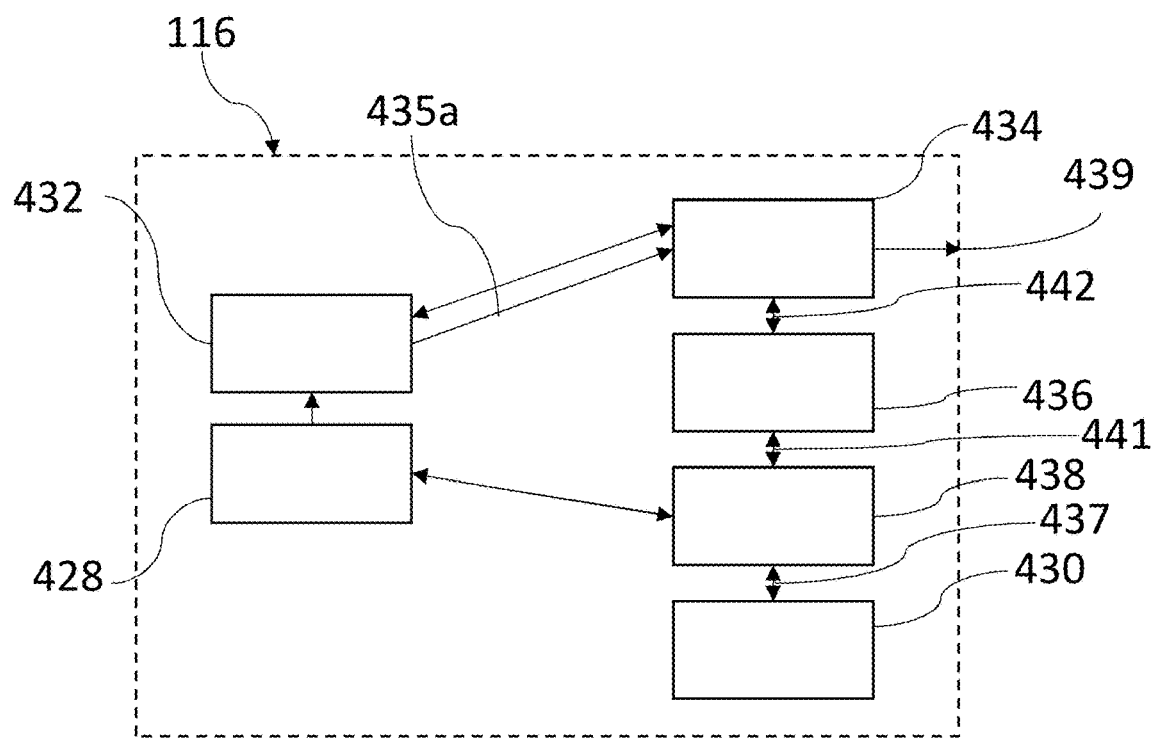
Figure 5:
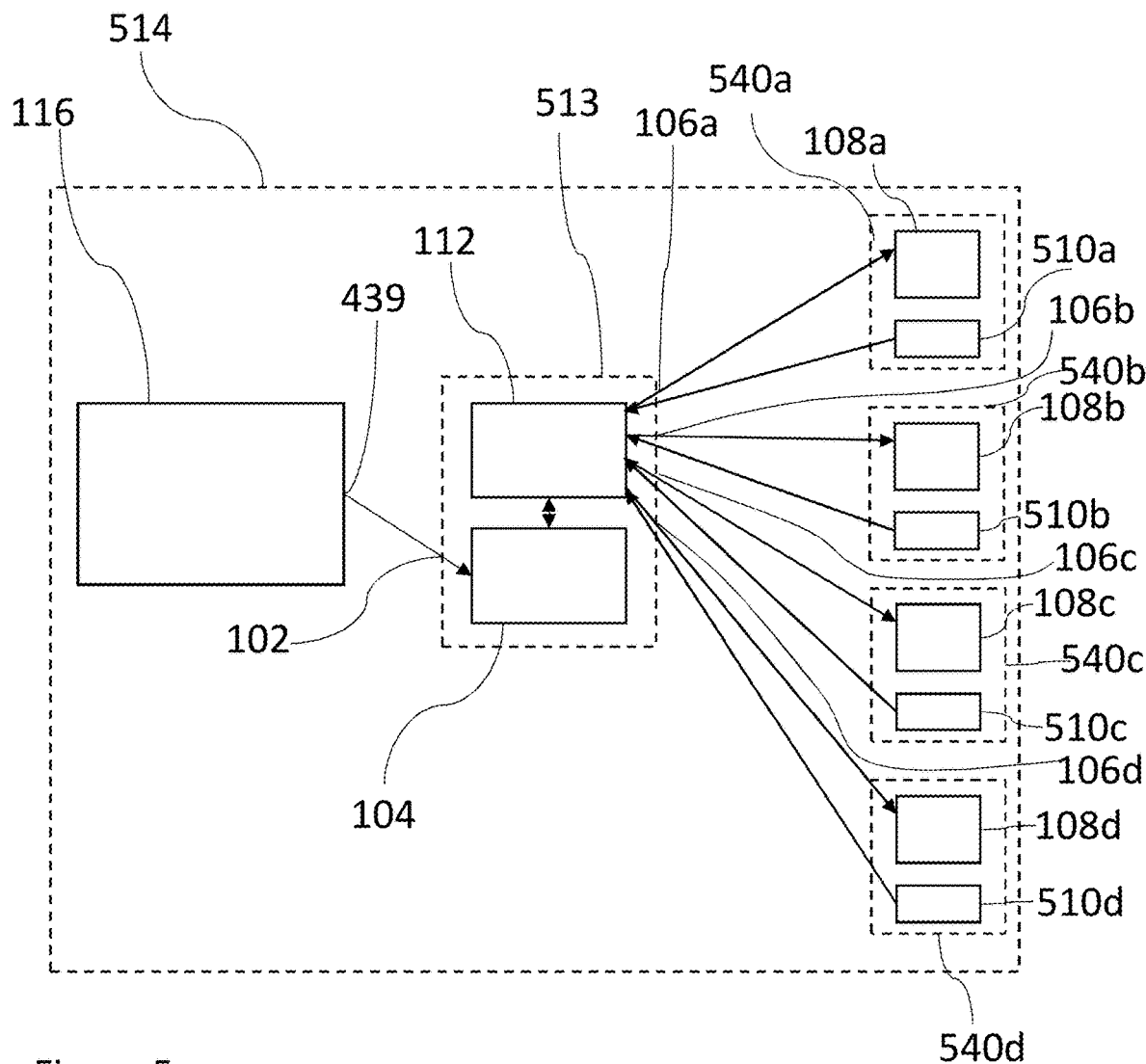
Figure 6:
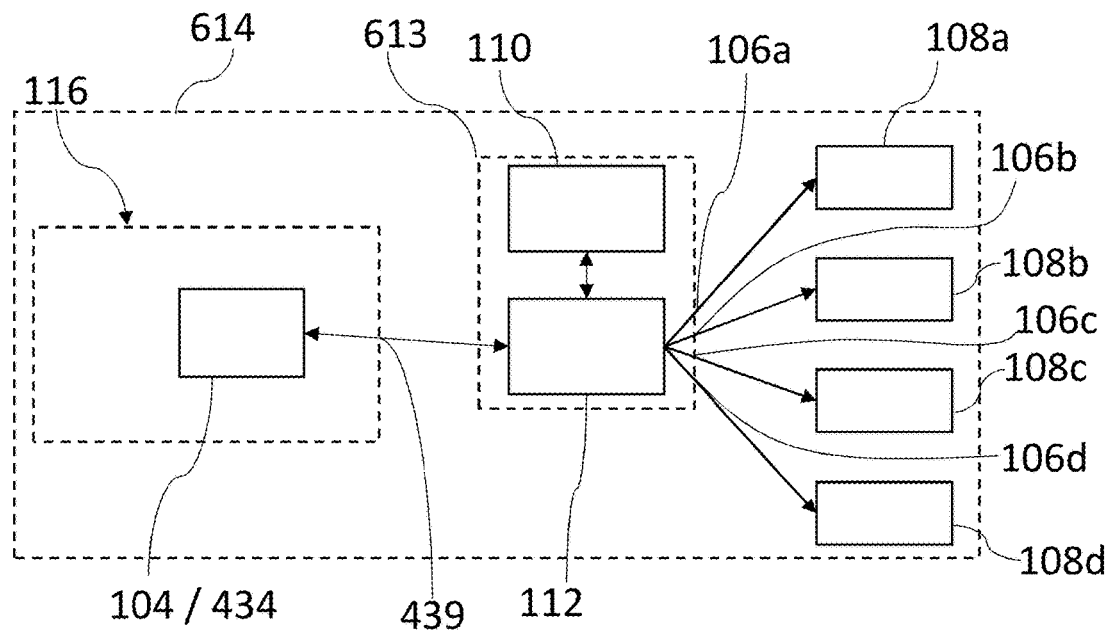
Figure 7:
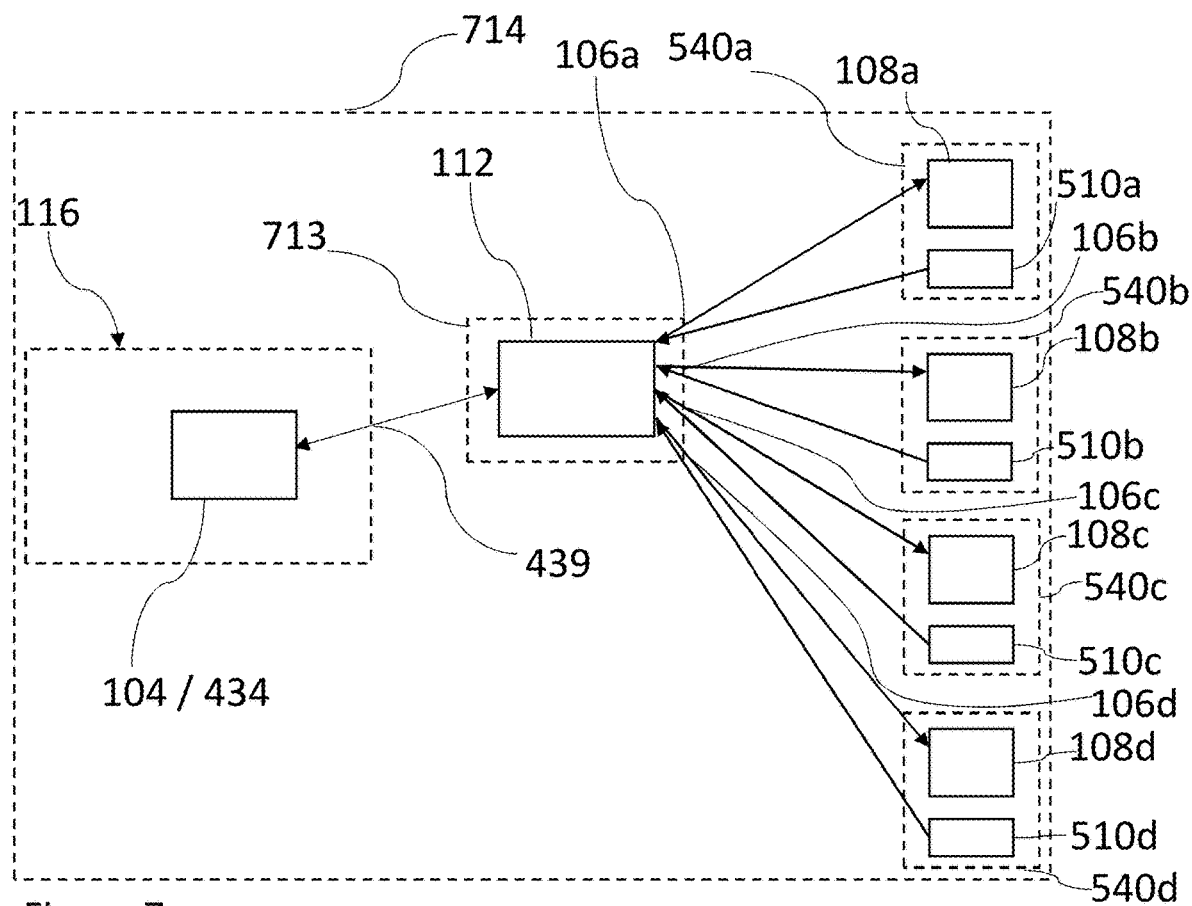
Figure 8:
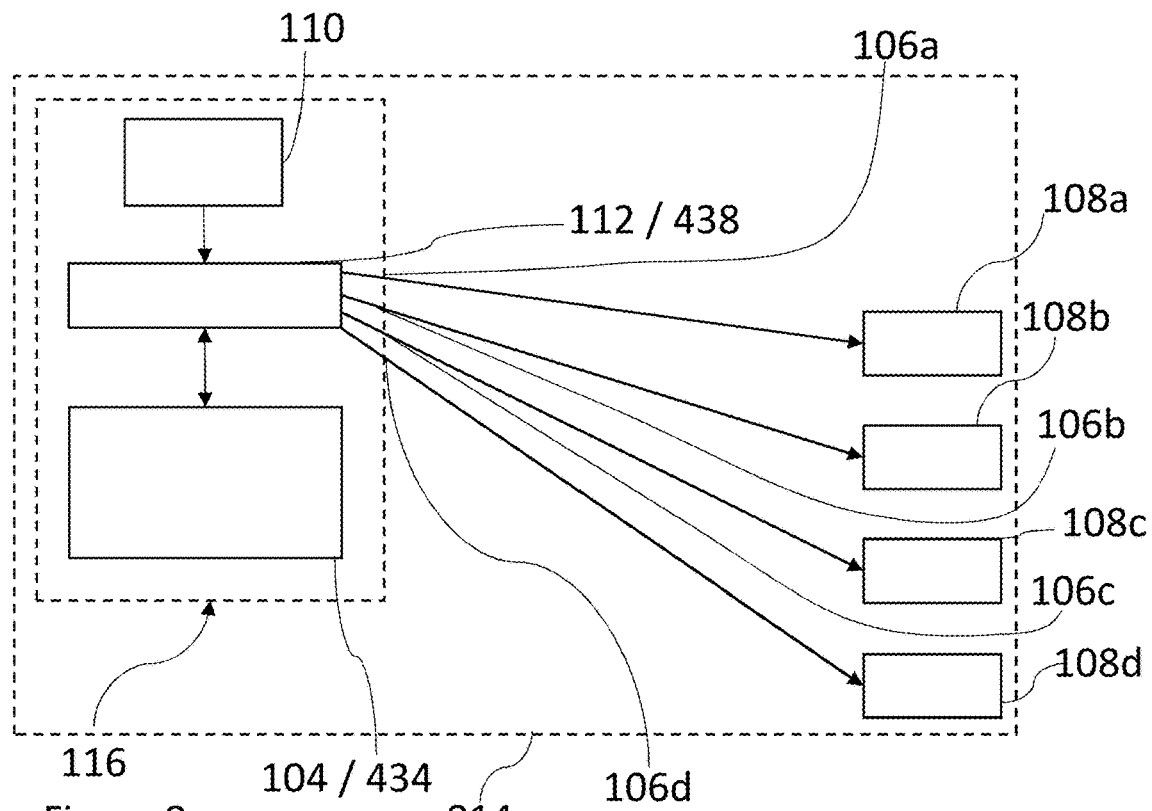
Figure 9:
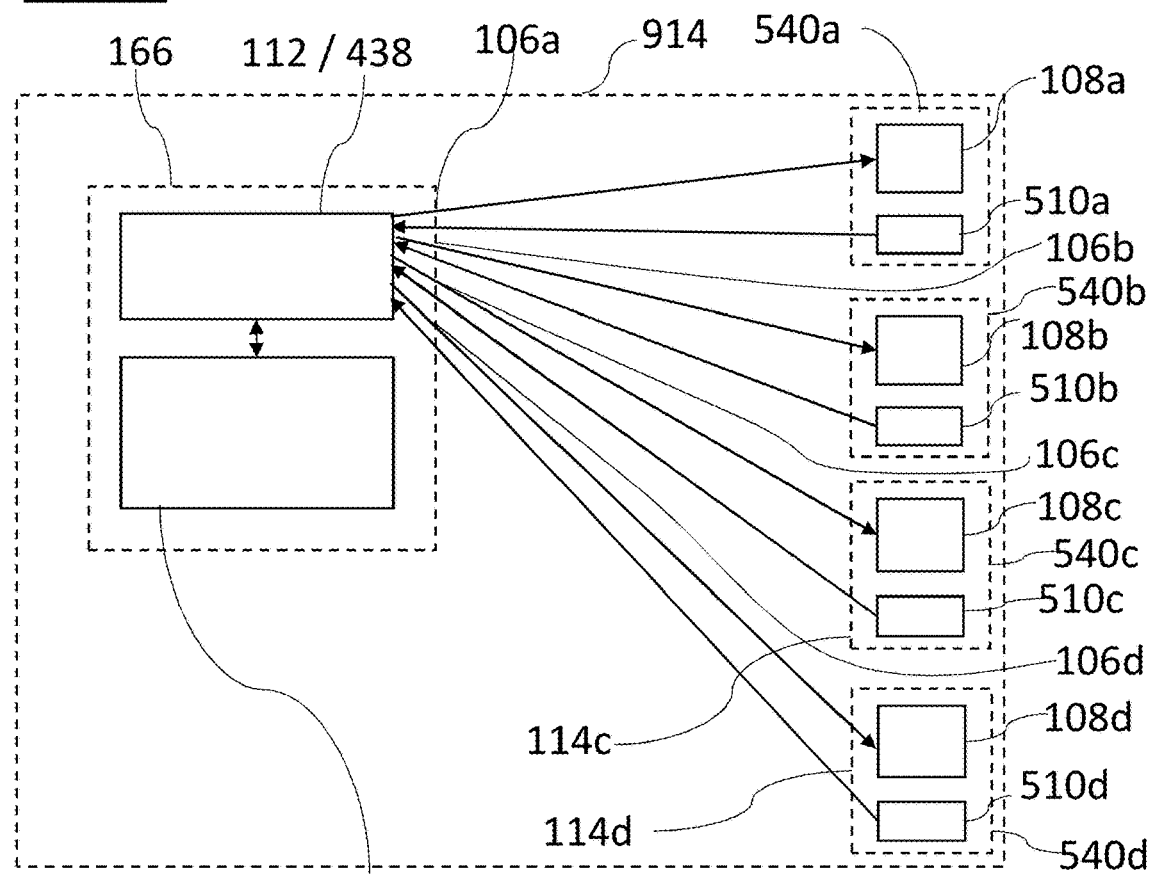
Figure 10A:
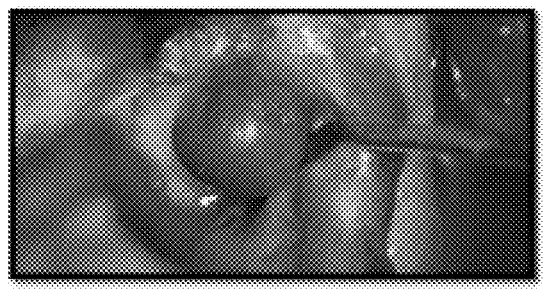
Figure 10B:
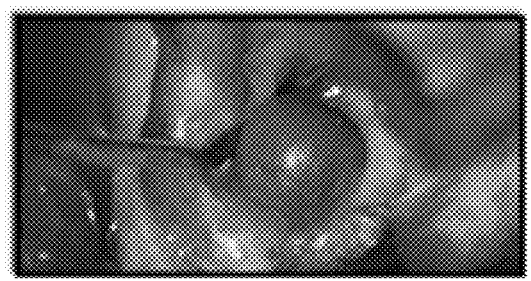
Figure 10C:
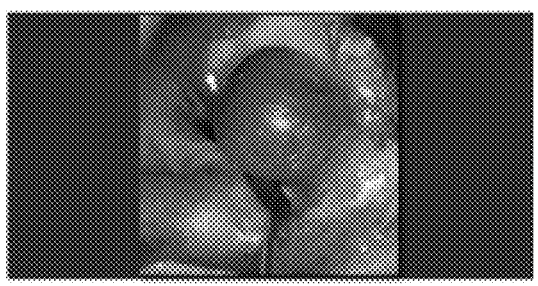
Figure 10D:
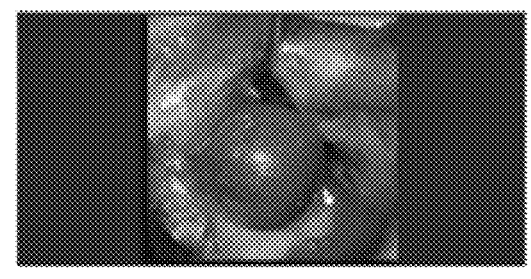
Figure 11:
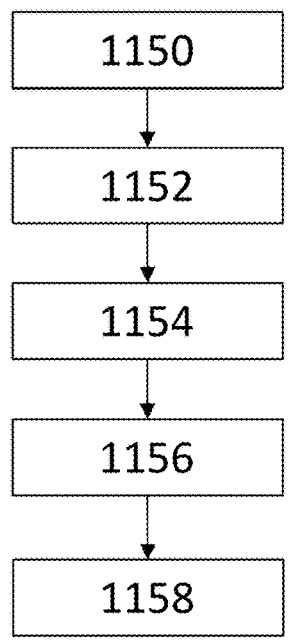

FIG. 1 is a schematic illustration of a first embodiment of medical imaging system according to the disclosed technology, FIG. 2 is a perspective illustration of the first embodiment of medical imaging control apparatus suitable for use in the medical imaging system illustrated in FIG. 1, FIG. 3 is a schematic illustration of an alternative embodiment of user interface suitable for use in the medical imaging control apparatus illustrated in FIG. 2, FIG. 4 is a schematic illustration of a microscope suitable for use in the medical imaging system illustrated in FIG. 1, FIG. 5 is a schematic illustration of an alternative embodiment of medical imaging system according to the disclosed technology, FIG. 6 is a schematic illustration of a further alternative embodiment of medical imaging system, according to the disclosed technology, FIG. 7 is a schematic illustration of a further alternative embodiment of medical imaging system, according to the disclosed technology, FIG. 8 is a schematic illustration of a further alternative embodiment of medical imaging system, according to the disclosed technology, FIG. 9 is a schematic illustration of a further alternative embodiment of medical imaging system, according to the disclosed technology, FIG. 10a is an example of an image generated using the medical imaging system illustrated in any of the above figures, wherein the angle of rotation is 0°, FIG. 10b is an example of an image generated using the medical imaging system illustrated in any of the above figures, wherein the angle of rotation is 180°, FIG. 10c is an example of an image generated using the medical imaging system illustrated in any of the above figures, wherein the angle of rotation is 90°, FIG. 10d is an example of an image generated using the medical imaging system illustrated in any of the above figures, wherein the angle of rotation is 270°, FIG. 11 is a schematic illustration of a method of operating a medical imaging system according to the disclosed technology.

DETAILED DESCRIPTION

Referring now to FIG. 1, there is shown a schematic illustration of one embodiment of medical imaging system 114 suitable for use in surgery.

The medical imaging system 114 includes a medical imaging control apparatus 100 having a data input interface 102 which is configured to receive electronic image data representing an original image of an object. The data input interface could be a port adapted to be connected to a removable data transfer cable, such as a HMDI, SDI or DP port. Alternatively the data input interface 102 could be a hard-wired connection between an electronic image generator such as a microscope computer system. Equally, the data input interface 102 could comprise a receiver suitable for receiving the electronic image data wirelessly. Similarly, any of the data output interfaces 106a, 106b, 106c, 106d could comprise a transmitter suitable for wireless transmission of electronic image data to a display device.

The medical imaging control apparatus 100 further comprises a processor 104 which is configured to process electronic image data received at the data input interface 102 such that when the electronic image data is used to generate an image the image generated is the original image rotated through a selected angle of rotation. The processor 104 may be configured to process the electronic image data such that when the electronic image data is used to generate an image, the image generated is the original image rotated through one a plurality of predetermined angles of rotation. In this embodiment, the processor 104 is configured to process the electronic image data such that when the processed electronic image data is used to generate an image, the image generated is the original image rotated through either 90°, 180°, or 270°.

The medical imaging control apparatus 100 also has a plurality of data output interfaces 106a, 106b, 106c, 106d via which processed electronic image data from the processor 104 can be provided to a display so that the processed electronic image data can be used to generate an image. In this particular embodiment, the medical imaging control apparatus 100 has four data output interfaces 106a, 106b, 106c, 106d.

The apparatus 100 may be configured to receive, process and transmit electronic image data representing a visible light image of an object, a fluorescent light image of an object, an ultra-violet light image of an object, or any combination thereof. In this embodiment, the data input interface 102 is configured to receive electronic image data which can be used to generate an image stream. The medical imaging control apparatus 100 can thus be used in relation to the display of video images.

The medical imaging control apparatus 100 is also provided with a user interface 110 which is configured with a plurality of user-selectable elements. The user-selectable elements are configured to be operable by a user to select one of the data output interfaces 106a, 106b, 106c, 106d and to assign to the user-selected data output interface 106a, 106b, 106c, 106d one of the predetermined angles of rotation.

The medical imaging control apparatus 100 further comprises a controller 112 configured to control the transmission of electronic image data via the user-selected data output interface 106a, 106b, 106c, 106d, wherein the electronic image data transmitted via the user-selected data output interface 106a, 106b, 106c, 106d has been processed by the processor 104 such that when the electronic image data is used to generate an electronic image the image generated is the original image rotated through the predetermined angle of rotation assigned to that user-selected data output interface 106a, 106b, 106c, 106d.

The electronic image data is typically an data array representing the color and brightness of each pixel in the image, scanning across the image from left to right, and top to bottom. The rotation may be carried out computationally, by applying a rotation matrix to the data array. In the case of the 180° rotation, this may be achieved by reflecting the image on two orthogonal axes—one axis extending from the top of the image to the bottom, and the other extending from the right side of the image to the left side.

The apparatus 100 could equally be configured to process the image data such that when it is received by the display 108a, 108b, 108c, 108d, the 180° rotation image is generated by assigning the data in the array to the pixels starting at the bottom right hand corner, and building up the image from right to left and bottom to top.

In this embodiment, the processor 104, controller 112, data input interface 102, data output interfaces 106a, 106b, 106c, 106d, and user interface 110 are arranged together in a control hub 113.

Referring now to FIG. 2, there is shown a perspective illustration of one embodiment of medical imaging control apparatus 100 suitable for use in the system illustrated in FIG. 1. In this embodiment the processor 104, user interface 110 and controller 112 are provided in a housing 222.

Also in this embodiment, the data input interface 102 comprises a port provided in the housing such as a HMDI, SDI, or DP port, and is configured to be connected to a data transfer cable 224. Each one of the data output interfaces 106a, 106b, 106c, 106d also comprises a port provided in the housing such as a HMDI, SDE or DP port, and is configured to be connected to a data transfer cable 224. It should be appreciated, however, that the data input interface 102 could comprise a receiver suitable for receiving the electronic image data wirelessly. Similarly, any of the data output interfaces 106a, 106b, 106c, 106d could comprise a transmitter suitable for wireless transmission of electronic image data to a display device.

In this particular embodiment the user interface 110 comprises a keypad, and the user-selectable elements 218a, 218b, 218c, 218d, 220a, 220b, 220c, 220d are keys or buttons on the keypad.

In this embodiment, each of a first set of the buttons 218a, 218b, 218c, 218d is associated with either one of the data output interfaces 106a, 106b, 106c, 106d, and each of a second set of the buttons 220a, 220b, 220c, 220d is associated with one of the predetermined angles of rotation. A user may therefore select one of the data output interfaces 106a, 106b, 106c, 106d by pressing one of the first set of buttons 218a, 218b, 218c, 218d, and assign one of the pre-determined angles of rotation to the selected data output interface 106a, 106b, 106c, 106d by pressing one of the second set of buttons 220a, 220b, 220c, 220d.

In one embodiment, the apparatus 100 may be configured such that the user selects the data output interface 106a 106b, 106c, 106d by pressing one of the first set of buttons 218a, 218b, 218c, 218d first, and then presses one of the second set of buttons 220a, 220b, 220c, 220d to assign one of the predetermined angles of rotation to the selected data output interface 106a, 106b, 106c, 106d. In another embodiment, the apparatus 100 is configured so that the user then presses one of the second set of buttons 220a, 220b, 220c, 220d first to select one of the predetermined angles of rotation, and then presses one of the first set of buttons 218a, 218b, 218c, 218d to select the data output interface 106a, 106b, 106c, 106d to which the selected angle of rotation is assigned.

Each button in the second set of buttons 220a, 220b, 220c, 220d may be arrow shaped or marked with an arrow, the relative directions of the arrows indicating the angle of rotation associated with that button 220a, 220b, 220c, 220d. This may provide the user with a particularly intuitive way of selecting the angle of rotation.

In this particular embodiment, the buttons 220a, 220b, 220c, 220d are arranged such that the arrows point in four different directions like the points of a compass, and the buttons will be herein forth referred to as the south button 220a, the north button 220b, the east button 220d and the west button 220c. In this example, the first set of buttons 218a, 218b, 218c, 218d are arranged in a row at an upper end of the housing 222, with the second set of buttons 220a, 220b, 220c, 220d below, with the north button 220b pointing towards the first set of buttons 218a, 218b, 218c, 218d, the south button 220a pointing in the opposite direction away from the first set of buttons 218a, 218b, 218c, 218d, the west button 220c pointing to the right at right angles to the north and south buttons 220b, 220a, and the east button 220d pointing to the left also at right angles to the north and south buttons 220b, 220a.

The second set of buttons 220a, 220b, 220c, 220d are configured so that the south button 220a is associated with an angle of rotation of zero degrees. In other words, when the user selects one of the data output interfaces 106a, 106b, 106c, 106d and then presses the south button 220a, the electronic image data transmitted to the display 108a, 108b, 108c, 108d connected to the selected data output interface 106a, 106b, 106c, 106d is such that when the electronic image data is used by the display to generate an electronic image, the image generated is the original image rotated through zero degrees (i.e. is the same as the original image).

The north button 220b is associated with an angle of rotation of 180°. In other words, when the user selects one of the data output interfaces 106a, 106b, 106c, 106d and then presses the north button 220b, the electronic image data transmitted to the display 108a, 108b, 108c, 108d connected to the selected data output interface 106a, 106b, 106c, 106d is such that when the electronic image data is used by the display 108a, 108b, 108c, 108d to generate and display an electronic image, the image displayed is the original image rotated through 180°.

The west button 220c is associated with an angle of rotation of 90° clockwise. In other words, when the user selects one of the data output interfaces 106a, 106b, 106c, 106d and then presses the west button 220c, the electronic image data transmitted to the display 108a, 108b, 108c, 108d connected to the selected data output interface 106a, 106b, 106c, 106d is such that when the electronic image data is used by the display 108a, 108b, 108c, 108d to generate and display an electronic image, the image displayed is the original image rotated through 90° clockwise.

The east button 220d is associated with an angle of rotation of 270° clockwise (or 90° anticlockwise). In other words, when the user selects one of the data output interfaces 106a, 106b, 106c, 106d and then presses the east button 220d, the electronic image data transmitted to the display 108a, 108b, 108c, 108d connected to the selected data output interface 106a, 106b, 106c, 106d is such that when the electronic image data is used by the display 108a, 108b, 108c, 108d to generate and display an electronic image, the image displayed is the original image rotated through 270° clockwise (or 90° anticlockwise).

It should be appreciated that the user-selectable elements need not comprise buttons. They may, for example, comprise icons on a touch sensitive screen, a voice activated input device, a gesture recognition control input device, a joystick, or any other suitable input device.

An example of a suitable configuration of touch sensitive screen is illustrated in FIG. 3. In this case, the first set of user-selectable elements 318a, 318b, 318c, 318d are labelled "Set 1", "Set 2", "Set 3" and "Set 4" and the second set of user-selectable elements 320a, 320b, 320c, 320d carry arrows which are arranged and configured in the same way as the second set of buttons 220a, 220b, 220c, 220d described above in relation to FIG. 2.

The processor 104 may be configured to process the electronic image data to change the brightness level of an image generated from the electronic image data. In this case, the user interface 108 further comprises brightness control elements 322a, 322b which are configured to be operable by a user to select a brightness level for the electronic image data to be transmitted via the user-selected data output interface 106a, 106b, 106c, 106d, and, the controller 112 is configured to control the transmission via the user-selected data output interface 106a, 106b, 106c, 106d of the electronic image data at the user-selected brightness level.

Examples of such brightness control elements 322a, 322b are illustrated in FIG. 3, and comprise two icons—one marked with an > symbol which is operable to increase the brightness level assigned to the user-selected data output interface 106a, 106b, 106c, 106d, and one marked with an < symbol which is operable to decrease the brightness level assigned to the user-selected data output interface 106a, 106b, 106c, 106d. In this embodiment, the user interface 106 also includes a display which indicates the brightness level assigned to the user-selected data output interface 106a, 106b, 106c, 106d.

Referring now to FIG. 4, there is shown a schematic illustration of an example of a microscope 116 suitable for use in the system 114 illustrated in FIG. 1. In this embodiment, the microscope 116 includes microscope settings 428 including the light collection and magnification lenses, an illumination system 430 which may comprise a light source and filters, and an observation system 432 which collects light from the microscope settings 428 and which comprises sensors which are configured to convert the light from the microscope settings 428 into an electronic signal or signals. The illumination system 430 is configured to illuminate an object to be viewed using the microscope 116, and the microscope settings used to collect light from the object. The light collected could be visible light, ultraviolet light or infrared light, any combination thereof. The sensors could be CCD (charge-coupled device) or CMOS (complementary metal-oxide semiconductor) image sensors, and may include sensors for detection of visible light, or NIR or UV sensors The observation system 432 may also comprise a beam splitter, and one or more filters.

The microscope 116 also has a computer system which comprises a microscope processor 434, a microscope controller interface 436 and a microscope controller 438. The sensors in the observation systems 432 are connected to the microscope processor 434 via at least one signal line 435a via which the electronic signals generated by the sensors are transmitted to the microscope processor 434. The microscope processor 434 is configured to process the electronic signals received from the observation system 432 to produce an electronic image signal suitable for use by an appropriate display to generate an image of the object. The microscope processor 434 is connected by a signal line to a microscope data output interface 439 via which electronic image signals generated by the microscope processor 343 may be transmitted to an appropriate display.

The microscope data output interface 439 is typically a port such as an HDMI, SDI or DP port, and which is configured to be connected to a display via a data transfer cable, but it could comprise a transmitter suitable for wireless transmission of electronic image data to a display device.

In this embodiment, the microscope controller 438 is connected to the illumination system 430 via a bidirectional signal line 437, and configured to control operation of the illumination system, for example the controlling intensity of light emitted by the light source, regulating any filters, or where the illumination system includes a plurality of light sources, controlling which light source is operational.

The microscope controller 438 is connected to the controller interface 436, and the controller interface 436 to the microscope processor 434 via further bidirectional signal lines 441, 442, by means of which setting data of the microscope (working distance, magnification, illumination system settings etc.) may be transmitted to the microscope processor 434.

All these features are all standard of digital microscopes, for example such as those used in microsurgery, but it should be appreciated that the any other configuration of microscope which has a data output interface by means of which electronic image signals can be transmitted to a display could equally be used in the system 114 described above in relation to FIG. 1.

The microscope data output interface 439 of such a microscope 116 is typically connected directly to a display, and the microscope 116 may thus be used by a surgeon during microsurgery to view a magnified image of the surgical field. The display may, for example, be a head-mounted display device such as the devices described in WO2018/170522, EP3848779, or WO2021/224404. In this case, the lead surgeon would typically wear the head-mounted display device.

In the system 114 described above in relation to FIG. 1, instead of being connected directly to a display, the microscope data output interface 439 is connected to the data input interface 102 of the medical imaging control apparatus 100. Typically, this is a wired connection made using an appropriate data transfer cable, but it could equally be a wireless connection.

Images from the microscope 116 can be viewed on all of the displays 108a, 108b, 108c, 108d connected to the data output interfaces 106a, 106b, 106c, 106d of the medical imaging control apparatus 100. Where the displays 108a, 108b, 108c, 108d are head-mounted display devices, the images from the microscope may be viewed by a plurality of different people. For example, the lead surgeon may wear one head-mounted device, an assistant surgeon another, and observers/students the others. By virtue of the use of the described medical imaging control apparatus 100, this is possible even where the microscope 116 only has a single data output interface 439.

Moreover, each wearer of one of the head-mounted display devices may use the medical imaging control apparatus 100 to select the orientation of the image generated by their particular display device to correspond to their position relative to the patient.

So, for example, the lead surgeon may choose to assign a 0° angle of rotation to the image transmitted to his/her head-mounted display device (e.g. by pressing the south button 220a, 320a in the embodiments illustrated in FIGS. 2 & 3). If the assistant surgeon is standing on the other side of the patient directly opposite and facing the lead surgeon, he/she may assign the 180° angle of rotation to the image signal transmitted to his/her head-mounted display device (e.g. by pressing the north button 220b, 320b in the embodiments illustrated in FIGS. 2 & 3). The image displayed in his/her head-mounted display device will thus have the same orientation as if he/her were looking directly at the patient.

Similarly, a wearer of a head-mounted display device standing at the left-hand side of and perpendicular to the lead surgeon, could choose to assign a 270° angle of rotation to the image transmitted to his/her head-mounted display device (e.g. by pressing the east button 220d, 320d in the embodiments illustrated in FIGS. 2 & 3), and a wearer of a head-mounted display device standing at the left-hand side of and perpendicular to the lead surgeon, could choose to assign a 90° angle of rotation to the image transmitted to his/her head-mounted display device (e.g. by pressing the west button 220c, 320c in the embodiments illustrated in FIGS. 2 & 3).

Examples of the images displayed on the various head-mounted display devices 540a, 540b, 540c, 540d are shown in FIGS. 10a, 10b, 10c, and 10d. FIG. 10a shows the image viewed by the lead surgeon, FIG. 10b shows the image seen by the assistant surgeon (a 180° rotation of the image seen the lead surgeon), FIG. 10c shows the image seen by the right-hand observer (a 90° clockwise rotation of the image seen by the lead surgeon), and FIG. 10d shows the image seen by the left-hand observer (a 270° clockwise rotation of the image seen by the lead surgeon).

Moreover, should the wearers of the head-mounted display devices change their position relative to the patient or lead surgeon during the surgical procedure, they could simply use the medical imaging control apparatus 100 to change the orientation of the image they see to correspond to the view from their new position.

Providing the medical imaging control apparatus 100 as a control hub 113, which can be connected to the data output interface of a standard microscope 116, is particularly convenient, as it may facilitate the viewing of the image from a standard microscope with a single date output interface 439 by a plurality of head-mounted display devices, and the control of the orientation of the image viewed through each device. It should be appreciated, however, that the medical imaging control apparatus 100 need not be configured in this way.

For example, the user interface 110 may comprise a plurality of interfaces provided on separate devices. For example, in the embodiment illustrated in FIG. 5, where each display 108a, 108b, 108c, 108d is provided by a head-mounted display device 540a, 540b, 540c, 540d, the user interface 110 may comprise a user interface 510a, 510b, 510c, 510d of each head-mounted display device 540a, 540b, 540c, 540d. For example, the user interface 100 may be provided by an eye-tracking control interface provided in each head-mounted display device 540a, 540b, 504c, 504d.

An example of this configuration of medical imaging system 514 is illustrated in FIG. 5. In this embodiment, the controller 112 and processor 104 are provided in the control hub 513, and instead of each of the user-selectable elements being associated with either one of the data output interfaces 106a, 106b, 106c, 106d or one of the predetermined angles of rotation, each user interface 510a, 510b, 510c, 510d has a set of user-selectable elements which are associated with one of the predetermined angles of rotation, and which are operable to assign the selected angle of rotation to the data output interface 106a, 106b, 106c, 106d to which the user interface 510a, 510b, 510c, 510d is connected. To facilitate this, there is a signal line between each head-mounted display device 540a, 540b, 540c, 540d and the control hub 513 which allows for the transmission of the control information generated by each user interface 510a, 510b, 510c, 510d (namely the selected angle of rotation) to the controller 112. In one embodiment, this is achieved by each of the data output interfaces 106a, 106b, 106c, 106d also functioning as a data input interface, and being connected to one of the head-mounted displays 540a, 540b, 540c, 540d via a bidirectional signal line.

It is also possible for the processing of the electronic image data required to rotate the image through the selected angle of rotation to be carried out by the microscope processor 434, in other words, for the processor 104 of the medical imaging control apparatus 100 to be the microscope processor 434. Examples of this embodiment are illustrated in FIGS. 6 and 7. In the medical imaging system 614 illustrated in FIG. 6, the user interface 110 and controller 112 of the medical imaging control apparatus 100 are provided in the control hub 613, whilst in the medical imaging system 714 illustrated in FIG. 7, only the controller 112 is provided in the control hub 713, the user interface being the user interfaces 510a, 510b, 510c, 510d of the head-mounted display devices 540a, 540b, 540c, 540d just as described above in relation to FIG. 5.

It will be appreciated that in both these embodiments, the data input interface of the image control apparatus is now, in effect, the interface between the signal line 435a from the microscope observation system 432 and the microscope processor 434. There must be a connection between the microscope processor 434 and the control hub 613/713 which allows for communication of control signals from the controller 112 to the microscope processor 434. In one embodiment, the microscope data output interface 439 is configured to also act as a data input interface, and is connected to the control hub 613/713 via a bi-directional signal line.

Alternatively, it is possible for the control hub to be omitted completely, and for all the parts of the medical imaging control apparatus to be provided as part of the microscope computer system.

In the embodiment of medical imaging system 814 illustrated in FIG. 8, the processing of the electronic image data required to rotate the image through the selected angle of rotation to be carried out by the microscope processor 434, in other words, for the processor 104 of the medical imaging control apparatus 100 to be the microscope processor 434, and the control function provided by the controller 112 of the medical imaging apparatus is carried out by the microscope controller 438. The microscope 116 is also provided with the user interface 110. In this embodiment, however, the microscope 116 has a plurality of data output interfaces 106a, 106b, 106c, 106d, one of the displays 108a. 108b, 108c, 108d being connected to each.

In a further alternative embodiment of medical imaging system 913 illustrated in FIG. 9, the processing of the electronic image data required to rotate the image through the selected angle of rotation is carried out by the microscope processor 434, in other words, for the processor 104 of the medical imaging control apparatus 100 is the microscope processor 434, and the control function provided by the controller 112 of the medical imaging apparatus is carried out by the microscope controller 438, but the user interface are the user interfaces 510a, 510b, 510c, 510d of the head-mounted display devices 540a, 540b, 540c, 540d just as described above in relation to FIG. 5 above. Again, the microscope 116 has a plurality of data output interfaces 106a, 106b, 106c, 106d, to each of which one of the displays 108a. 108b, 108c, 108d is connected.

It should be appreciated that the medical imaging control apparatus 100 described above need not be configured to allow the user to select between angles of rotation of 90°, 180° and 270°. It may be configured from different angles of rotation, or from more or less than three different angles of rotation. Equally, the medical imaging control apparatus 100 need not be configured to allow the used to select between a plurality of pre-determined angles of rotation. The user interface 110 may be configured to allow a user to enter any angle of rotation, and the processor 104 configured to process the electronic image data received at the data input interface 102 such that when the electronic image data is used to generate an image the image generated is the original image rotated through the angle of rotation entered by the user. In this case, the user-selectable elements may comprise number keys (on a keyboard, keypad or touchscreen), or the user interface 110 may be configured with appropriate voice or gesture recognition capability to enable a user to enter any number up to 360.

As mentioned above, the apparatus 100 may be configured to receive, process and transmit electronic image data representing a visible light image of an object, a fluorescent light image of an object, an ultra-violet light image of an object, or any combination thereof.

Similarly, the electronic image data may include derived from a source other than the microscope 116. For example, it may include image data from an MRI or X-ray image taken of the patient before commencement of the surgery. This pre-op image data could be combined with the image data derived from the microscope 116 to generate an image representing the light image of the surgical site during the operation overlaid with the pre-op image. Alternatively or additionally it could include image date from another source such as an endoscope, a blood pressure/flow monitoring system, or a surgical process guidance system, which image data would also be over laid on the image derived from the microscope 116. In these cases, the combination of the image data from the microscope 116 and the other image data could be carried out by the microscope processor 434, and the combined image data delivered to the data input interface 102. Alternatively, in relation to the embodiments illustrated in FIGS. 1 and 5, the other image data could be transmitted to the control hub 113, 513, and combined with the image data from the microscope 116 by the processor 104 of the medical imaging control apparatus 100.

The apparatus 100 may also be configured to allow a user to choose which sort of image data is transmitted to the selected data output interface 106a, 106b, 106c, 106d. For example, the user interface 110 may comprise user-selectable elements which allow the user to select a visible light image, a fluorescent light image, an ultra-violet light image, a combination of these images, and assign the selected image type to the user-selected date output interface 106a, 106b, 106c, 106d, and the controller 112 configured to control transmission of the appropriate electronic image data to the selected data output interface 106a, 106b, 106c, 106d. The user interface 110 may, for example, have "UV", "VL" and "FL" buttons to which are operable to allow the user to select electronic image data representing an ultra-violet light image, a visible light image, or a fluorescent light image, or any combination thereof, and to assign the selected image type to the selected data output interface 106a, 106b, 106c, 106d. Similarly, the user interface 110 may comprise user-selectable elements which allow a user to select other image data (MRI/X-Ray/blood pressure etc.) to be combined with the microscope image data sent to the selected data output interface 106a, 106b, 106c, 106, and the controller 112 configured to control transmission of the appropriate electronic image data to the selected data output interface 106a, 106b, 106c, 106d.

The description above relates to a monocular microscope, but it should be appreciated that the microscope 116 may be a stereo microscope. A stereo microscope collects light from the object along two different light paths, and a separate image, representing the object from a slightly different view point, is presented to each eye of the observer via a head-mounted display device. In other words, a right-hand image is presented to the right eye of the wearer of the head-mounted display device, and a left-hand image is presented to the left eye of the wearer of the head-mounted display device. The electronic image data transmitted to the display 108a, 108b, 108c, 108d therefore comprises two slightly different images.

Where the microscope 116 is a stereo microscope, the same devices and processes may be applied, but with electronic image data required to display right hand and left hand images being sent to the data output interfaces 106a, 106b, 106c, 106d to which 0° and 180° angles of rotation have been assigned, so that stereoscopic images of the surgical site can be viewed the lead surgeon and assistant surgeon. In relation to the image data sent to the data output interface 106a, 106b, 106c, 106d connected to the assistant surgeon's head-mounted display device 540a, 504b, 540c, 504d, the medical imaging control apparatus 100 is configured not only to process the image data so that the two images correspond to 180° rotations of the original right hand and left hand images, but also to swap the images so that the rotated right hand image is presented to the left eye of the assistant surgeon, and the rotated left hand image is presented to the right eye of the assistant surgeon, to maintain the stereoscopic view.

In the case of the head-mounted display devices 540a, 540b, 540c, 504d connected to data output interfaces 106a, 106b, 106c, 106d to which 90° and 270° angles of rotation have been assigned, the same image is presented to both eyes of the wearer. This may be achieve by sending the image data required to generate an image corresponding to a 90° or 270° rotation of only one of the right hand or left hand images to the head-mounted display device 540a, 540b, 540c, 540d, and the same image presented to both eyes of the wearer. As such, observers standing to the right and left of the lead surgeon will not, therefore, have a stereoscopic view.

It will be appreciated that the medical imaging control apparatus 100 can be used to implement a method of operating a medical imaging system comprising the steps of acquiring electronic image data (in these embodiment, the image data generated by a microscope 116) representing an original image of an object, allowing a user to select one of a plurality of data output interfaces and to assign to the selected data output interface an angle of rotation, processing the image data such that when the processed image data is used to generate an image, the image generated is the original image rotated through the selected angle of rotation assigned to the user-selected data output interface, and transmitting the processed image data to the user-selected data output interface. The processed image data may be transmitted to a display 108a, 108b, 108c, 108d, and used by the display 108a, 108b, 108c, 108d to generate an display an image of the object.

One embodiment of this method is illustrated schematically in FIG. 11. This shows the following method steps:

a) acquiring electronic image data representing an original image of an object 1150,
b) a user selecting one of a plurality of data output interfaces 1152,
c) the user assigning to the selected data output interface an angle of rotation 1154, d) processing the image data such that when the processed image data is used to generate an image, the image generated is the original image rotated through the predetermined angle of rotation assigned to the user-selected data output interface 1156, and e) transmitting the processed image data to the user-selected data output interface 1158.

It should be appreciated that these method steps need not be carried out in this order. For example, the medical imaging control apparatus 100 might be configured as described in relation to FIG. 2 above to allow a user to select the angle of rotation before selecting the data output interface 106*a*, 106*b*, 106*c*, 106*d* to which the selected angle is assigned.

Moreover, the step of acquiring electronic image data could be carried out after the user has selected the data output interface 106*a*, 106*b*, 106*c*, 106*d* and angle of rotation, i.e. step 1150 carried out after step 1152, 1154.

These method can be implemented by use of a computer program product comprising program code stored on a machine-readable medium, the computer program being configured to carry out the method, when the computer program runs on a computer system of a medical imaging system, for example the computer system of a microscope 116 as described in relation to FIGS. 8 and 9 above.

Some embodiments relate to a medical imaging system 114, 514, 614, 714, 814, 914 comprising a microscope 116 as described in connection with one or more of the FIGS. 1 and 5 to 9. The microscope may be part of or connected to a computer system as described in connection with one or more of the FIGS. 1 to 9. FIGS. 1 and 5 to 9 show a schematic illustration of a medical imaging system 114, 514, 614, 714, 814, 914 configured to perform a method described herein. The microscope 116 is configured to take images and is connected to the computer system. The computer system is configured to execute at least a part of a method described herein. The computer system may be configured to execute a machine learning algorithm. The computer system and microscope 116 may be separate entities but can also be integrated together in one common housing. The computer system may be part of a central processing system of the microscope 116 and/or the computer system may be part of a subcomponent of the microscope 116, such as a sensor, an actor, a camera or an illumination unit, etc. of the microscope 116.

The computer system may be a local computer device (e.g. personal computer, laptop, tablet computer or mobile phone) with one or more processors and one or more storage devices or may be a distributed computer system (e.g. a cloud computing system with one or more processors and one or more storage devices distributed at various locations, for example, at a local client and/or one or more remote server farms and/or data centers). The computer system may comprise any circuit or combination of circuits. In one embodiment, the computer system may include one or more processors which can be of any type. As used herein, processor may mean any type of computational circuit, such as but not limited to a microprocessor, a microcontroller, a complex instruction set computing (CISC) microprocessor, a reduced instruction set computing (RISC) microprocessor, a very long instruction word (VLIW) microprocessor, a graphics processor, a digital signal processor (DSP), multiple core processor, a field programmable gate array (FPGA), for example, of a microscope or a microscope component (e.g. camera) or any other type of processor or processing circuit. Other types of circuits that may be included in the computer system may be a custom circuit, an application-specific integrated circuit (ASIC), or the like, such as, for example, one or more circuits (such as a communication circuit) for use in wireless devices like mobile telephones, tablet computers, laptop computers, two-way radios, and similar electronic systems. The computer system may include one or more storage devices, which may include one or more memory elements suitable to the particular application, such as a main memory in the form of random access memory (RAM), one or more hard drives, and/or one or more drives that handle removable media such as compact disks (CD), flash memory cards, digital video disk (DVD), and the like. The computer system may also include a display device, one or more speakers, and a keyboard and/or controller, which can include a mouse, trackball, touch screen, voice-recognition device, or any other device that permits a system user to input information into and receive information from the computer system.

Some or all of the method steps may be executed by (or using) a hardware apparatus, like for example, a processor, a microprocessor, a programmable computer or an electronic circuit. In some embodiments, some one or more of the most important method steps may be executed by such an apparatus.

Depending on certain implementation requirements, embodiments of the invention can be implemented in hardware or in software. The implementation can be performed using a non- transitory storage medium such as a digital storage medium, for example a floppy disc, a DVD, a Blu-Ray, a CD, a ROM, a PROM, and EPROM, an EEPROM or a FLASH memory, having electronically readable control signals stored thereon, which cooperate (or are capable of cooperating) with a programmable computer system such that the respective method is performed. Therefore, the digital storage medium may be computer readable.

Some embodiments according to the invention comprise a data carrier having electronically readable control signals, which are capable of cooperating with a programmable computer system, such that one of the methods described herein is performed.

Generally, embodiments of the present invention can be implemented as a computer program product with a program code, the program code being operative for performing one of the methods when the computer program product runs on a computer. The program code may, for example, be stored on a machine readable carrier.

Other embodiments comprise the computer program for performing one of the methods described herein, stored on a machine readable carrier.

In other words, an embodiment of the present invention is, therefore, a computer program having a program code for performing one of the methods described herein, when the computer program runs on a computer.

A further embodiment of the present invention is, therefore, a storage medium (or a data carrier, or a computer-readable medium) comprising, stored thereon, the computer program for performing one of the methods described herein when it is performed by a processor. The data carrier, the digital storage medium or the recorded medium are typically tangible and/or non-transitionary. A further embodiment of the present invention is an apparatus as described herein comprising a processor and the storage medium.

A further embodiment of the invention is, therefore, a data stream or a sequence of signals representing the computer program for performing one of the methods described herein. The data stream or the sequence of signals may, for example, be configured to be transferred via a data communication connection, for example, via the internet.

A further embodiment comprises a processing means, for example, a computer or a programmable logic device, configured to, or adapted to, perform one of the methods described herein.

A further embodiment comprises a computer having installed thereon the computer program for performing one of the methods described herein.

A further embodiment according to the invention comprises an apparatus or a system configured to transfer (for example, electronically or optically) a computer program for performing one of the methods described herein to a receiver. The receiver may, for example, be a computer, a mobile device, a memory device or the like. The apparatus or system may, for example, comprise a file server for transferring the computer program to the receiver.

In some embodiments, a programmable logic device (for example, a field programmable gate array) may be used to perform some or all of the functionalities of the methods described herein. In some embodiments, a field programmable gate array may cooperate with a microprocessor in order to perform one of the methods described herein. Generally, the methods are preferably performed by any hardware apparatus.

As used herein the term "and/or" includes any and all combinations of one or more of the associated listed items and may be abbreviated as "/".

Although some aspects have been described in the context of an apparatus, it is clear that these aspects also represent a description of the corresponding method, where a block or device corresponds to a method step or a feature of a method step. Analogously, aspects described in the context of a method step also represent a description of a corresponding block or item or feature of a corresponding apparatus.

LIST OF REFERENCE SIGNS

100—medical imaging control apparatus 102—data input interface
104—processor
106a, 106b, 106c, 106d—data output interface
108a, 108b, 108c, 108d—display 110—user interface
112—controller
113—control hub
114—medical imaging system
116—microscope
218a, 218b, 218c, 218d—user-selectable element
220a, 220b, 220c, 220d—user-selectable element
222—housing
224—data transfer cable
318a, 318b, 318c, 318d—user-selectable element
320a, 320b, 320c, 320d—user-selectable element
322a, 322b—brightness level control element
428—microscope settings
430—illumination system
432—observation system
434—microscope processor
435a, 435b—signal line
436—microscope controller interface
437—signal line
438—microscope controller
439—microscope data output interface
441—signal line
442—signal line
444—signal line
510a, 510b, 510c, 510d—eye tracking user interface
513—control hub
514—medical imaging system
540a, 540b, 540c, 540d—head-mounted display device
613—control hub
614—medical imaging system
713—control hub
714—medical imaging system
814—medical imaging system
914—medical imaging system
1150—step of acquiring electronic image data
1152—step of selecting one of a plurality of data output interfaces
1154—step of assigning to a selected data output interface an angle of rotation
1156—step of processing image data
1158—step of transmitting processed image data

What is claimed is:

1. A medical imaging control apparatus comprising:
 a. a data input interface which is configured to receive electronic image data representing an original image of an object;
 b. a processor which is configured to process the electronic image data received at the data input interface such that when the electronic image data is used to generate an image the image generated is the original image rotated through one of a plurality of predetermined angles of rotation;
 c. a plurality of data output interfaces via which processed electronic image data from the processor can be provided to a display so that the processed electronic image data can be used to generate an image;
 d. a user interface having a first set of user-selectable elements which are each associated with a respective one of the plurality of data output interfaces and which are configured to be operable by a user to select one of the plurality of data output interfaces and a second set of user-selectable elements which are each associated with a respective one of the plurality of predetermined angles of rotation and which are configured to be operable by a user to select one of the plurality of predetermined angles of rotation and to assign to the user-selected data output interface the user-selected angle of rotation;
 e. a controller configured to control the transmission of electronic image data via the user-selected data output interface, wherein the electronic image data transmitted via the user-selected data output interface has been processed by the processor such that when the electronic image data is used to generate an electronic image the image generated is the original image rotated through the user-selected angle of rotation assigned to that user-selected data output interface; and
 f. a housing;
 wherein the processor, the user interface, and the controller are provided in the housing.

2. The medical imaging control apparatus according to claim 1, wherein the processor is configured to process the electronic image data to change the brightness level of an image generated from the electronic image data, the user interface further comprises a brightness control element which is configured to be operable by a user to select a brightness level for the electronic image data to be transmitted via the user-selected data output interface, and the controller is configured to control the transmission via the user-selected data output interface of the electronic image data at the user-selected brightness level.

3. The medical imaging control apparatus according to claim 1, wherein the processor is configured to process the electronic image data received at the data input interface to generate an image stream.

4. The medical imaging control apparatus according to claim 1, wherein the data input interface comprises a port provided in the housing and is configured to be connected to a data transfer cable.

5. The medical imaging control apparatus according to claim 1, wherein the plurality of data output interfaces each comprises a respective port provided in the housing and is configured to be connected to a data transfer cable.

6. The medical imaging control apparatus according to claim 1, further comprising a second user interface provided on a device separate from the housing.

7. A medical imaging system comprising:
   a medical imaging control apparatus according to claim 1; and
   a microscope, wherein the data input interface of the medical imaging control apparatus is connected to the microscope such that electronic image data generated by the microscope is received by the data input interface of the medical imaging control apparatus.

8. The medical imaging system according to claim 7, further comprising a plurality of displays each of which is connected to one of the plurality of data output interfaces of the medical imaging control apparatus and configured to receive electronic image data from the data output interface to which such display is connected to use the received electronic image data to generate an image or an image stream.

9. The medical imaging system according to claim 8, wherein each of the plurality of displays is part of a head-mounted display device.

10. A medical imaging system comprising:
    a medical imaging control apparatus according to claim 1; and
    a plurality of displays each of which is connected to one of the plurality of data output interfaces of the medical imaging control apparatus and configured to receive electronic image data from the data output interface to which such display is connected to use the received electronic image data to generate an image or an image stream.

11. The medical imaging system according to claim 10, wherein each of the plurality of displays is part of a head-mounted display device.

12. A method of operating a medical imaging system comprising:
    acquiring electronic image data representing an original image of an object;
    enabling a user to select one of a plurality of data output interfaces by selecting one of a first set of user-selectable elements provided on a housing;
    enabling the user to assign to the user-selected data output interface one of a plurality of predetermined angles of rotation by selecting one of a second set of user-selectable elements provided on the housing;
    processing the electronic image data such that when the processed electronic image data is used to generate an image the image generated is the original image rotated through the predetermined angle of rotation assigned to the user-selected data output interface; and
    transmitting the processed image data to the user-selected data output interface.

13. A computer program product comprising program code stored on a machine-readable medium, the computer program code being configured to carry out the method of claim 12 when the computer program code runs on a computer system of a medical imaging system.

* * * * *